United States Patent [19]

Ellis et al.

[11] Patent Number: 4,543,359

[45] Date of Patent: Sep. 24, 1985

[54] TREATING CARDIAC ARRHYTHMIAS WITH DANTROLENE SODIUM

[75] Inventors: Keith O. Ellis; Alan F. Moore, both of Norwich, N.Y.

[73] Assignee: Eaton Laboratories, Inc., Manati, P.R.

[21] Appl. No.: 534,865

[22] Filed: Sep. 27, 1983

Related U.S. Application Data

[63] Continuation-in-part of Ser. No. 432,348, Oct. 1, 1982, abandoned.

[51] Int. Cl.[4] .............................................. A61K 31/415
[52] U.S. Cl. .................................... 514/390; 548/309
[58] Field of Search .................... 424/273 R; 514/390

[56] References Cited

PUBLICATIONS

Malloy, K., Ph.D. Thesis, Univ. of Rochester, 1981.
*Dissertation Abstracts International*, 42(8), 3222-B, (1982), [Salata, J., Ph.D. Thesis, 1981].
*Dissertation Abstracts International*, 42(4), 1337-B, (1981), [Malloy, K., PH.D. Thesis, 1981].
Salata, J. et al., *J. Pharmacol. Exp. Ther.*, 220(1), 157-166, (1982).

*Primary Examiner*—Richard A. Schwartz
*Attorney, Agent, or Firm*—Milton B. Graff, IV; Jack D. Schaeffer; Richard C. Witte

[57] ABSTRACT

Dantrolene sodium is useful as a cardiac antiarrhythmic agent in hypothermic and normothermic warm-blooded animals.

4 Claims, No Drawings

TREATING CARDIAC ARRHYTHMIAS WITH DANTROLENE SODIUM

This application is a continuation-in-part of application Ser. No. 432,348 filed Oct. 1, 1982, now abandoned.

This invention relates to the use of dantrolene sodium in the treatment of cardiac arrhythmias in hypothermic and normothermic warm-blooded animals.

Dantrolene sodium (1-[[5-(p-nitrophenyl) furfurylidene]-amino]hydantoin sodium salt) is described in U.S. Pat. No. 3,415,821. It is used as a skeletal muscle relaxant particularly in controlling the manifestations of clinical spasticity resulting from upper neuron disorders (Physicians' Desk Reference, 36th Edition, 1982). It is also used in the prevention and treatment of malignant hyperthermia in humans (Friesen et al., Can. Anaesth. Soc. J. 26:319-321, 1979). In connection with the use of dantrolene sodium in hyperthermic crisis it was observed that there was an elimination of the arrhythmias accompanying such crisis [Salata et al., Effects of Dantrolene Sodium on the Electrophysiological Properties of Canine Cardiac Purkinje Fibers, J. Pharmacol. Exp. Ther. 220(1):157–166 (Jan.) 1982] incorporated herein by reference.

It has now been discovered that dantrolene sodium prevents or reduces arrhythmia in hypothermic and normothermic warm-blooded animals. In particular, dantrolene sodium is effective in the treatment of supraventricular tachycardias, in suppressing slow responses in infarcted tissues and in abolishing ventricular premature beats or tachycardias originating in these tissues, and in correcting ventricular rhythm disturbances due to reentry.

Tests in experimental animals to assess the antiarrhythmic qualities of dantrolene sodium support the observation of such effects in patients affected with cardiac arrhythmia. Thus, in mice protection against cardiac dysrhythmias and fibrillation induced by the inhalation of chloroform was obtained.

For test purposes, dantrolene sodium was dispersed in 0.5% methocel to give doses of 3, 10, 30, 56, 100, 300 and 1000 mg/kg by introperitoneal injection to groups of 15 mice. Vehicle was similiarly given to a group of 30 mice. Sixty minutes after the treatment, mice were placed in a covered beaker containing chloroform soaked cotton. As soon as respiratory arrest occurred, the mice were withdrawn from the beaker and the thorax and pericardium were opened to expose the heart. The mice having neither ventricular fibrillation nor cardiac dysrthythmia were considered to be protected by the treatment from chloroform's arrhythmogenic effect. Data were evaluated with a computerized probit analysis to estimate the relationship between protection against dysrhythmias and $\log_{10}$ dose of drug and also the dose of dantrolene sodium required to protect 50% of a group of mice from chloroform-induced cardiac arrhythmias ($ED_{50}$).

Results for experiments testing dantrolene sodium and comparing its effects with four reference antiarrhythmic agents are summarized in Table 1. The lower and upper fiducial limits for dantrolene sodium's $ED_{50}$, 53 mg/kg (158 μmol/kg) ip, were, respectively, 19 and 139 mg/kg (56–413 μmol/kg). This range is similar to the range of dantrolene sodium effecting skeletal muscle relaxation in mice.

As was expected, known anti-arrhythmic drugs—lidocaine, procainamide and quinidine—tested in a similar manner effected a dose-dependent protection against arrhythmias as suggested in the literature. On the other hand, test (10, 30, 45 and 67 mg/kg) doses of verapamil, a calcium antagonist, did not reduce the incidence of dysrhythmias but did elicit signs of acute toxicosis.

TABLE 1

SUMMARY
Capacity of Dantrolene Sodium and Four Reference Anti-Arrhythmic Drug Pretreatments to Protect Groups (N = 12–16/Test Dose) of Mice from Chloroform Inhalation-Induced Cardiac Dysrhythmias

| Compound (Molecular Weight g/mole) | Pretreatment Time (min) | Pretreatment $ED_{50}{}^a$ (mg/kg) 95% Fiducial Limits | | |
|---|---|---|---|---|
| | | Mean | Lower | Upper |
| Dantrolene Sodium (336.25) | 60 | 53 | 19 | 139 |
| Procainamide HCL (271.79) | 15 | 114 | —$^b$ | 223 |
| Lidocaine (234.33) | 15 | 63 | 43 | 131 |
| Verapamil | 30 | No significant dose-related protection at subliminal toxic doses | | |
| Quinidine Sulfate (782.93) | 30 | 88 | 72 | 115 |

$^a$Dose of test compound, injected introperitoneally before subjection of mice to chloroform-inhalation, estimated by probit analysis to protect 50% of a group from chloroform-induced cardiac dysrhythmias.
$^b$Value ≦0 and without meaning.

Using the dog as the experimental model, similar results to those demonstrated in mice were secured.

A conscious dog model of cardiac arrhythmias was prepared by ligating for 60 minutes and then re-establishing patency of the left coronary artery. At about 24 hours after preparative surgery, dogs having a frequency of arrhythmias equal to or greater than 50% were treated with dantrolene sodium, 10 mg/kg. A 0.5 mg/ml solution of drug, prepared using the standard mannitol/NaOH solution (vehicle), was used for the study. Other dogs were given the vehicle, 20 ml/kg, as a negative control or lidocain HCl, 4 mg/kg, as a positive control. Dantrolene sodium and vehicle treatments were infused intravenously at a rate of approximately 15.3 ml/min. Lidocain HCl was slowly injected as a bolus over a period ≦2 min. Deviations in total ventricular contractions per minuts (TVC) and in ectopic ventricular contractions, expressed as a % of TVC (%EC) were monitored during a 120 minute post-treatment period in 3 groups of 5 dogs.

Control treatment effects were essentially as projected. In terms of overall means deviation from 5 to 120 min post-treatment, the effects of vehicle on TVC (−6.5±2.2, Mean±S.E.) and %EC (−0.3±1.8%) were null (P>0.05). Likewise, lidocaine HCl from 5 to 120 min post-treatment had no effect on TVC (−1.9±1.7) or %EC (0.0±2.4). However, between 2 and 4 min post-treatment, lidocaine HCl effected significant reductions (p>0.05) in %EC below pretreatment levels. The mean maximum reduction in %EC was −56±12%.

The dantrolene sodium-treated dogs, the overall means deviation in TVC (−4.1±2.3) for 5 through 120 min post-treatment was essentially null. However, a systematic, time-dependent reduction in %EC commenced at 5 min post-treatment, reached a maximum level ($-46\pm5\%$) between 10 and 90 min post-treatment, and was still apparent at 120 min post-treatment. The mean maximum reduction in %EC was not different from the mean maximum reduction elicited by lidocaine HCl at 2–4 min post-treatment. In the dantrolene sodium-treated group, the overall mean deviation in %EC ($-20.3\pm2.6\%$) for 5–120 min post-treatment was highly significant ($p<0.01$), as compared with corresponding means for the vehicle-and lidocaine HCl-treating groups.

The time-dependent reduction in %EC without a concomitant reduction in TVC indicated that dantrolene sodium like lidocaine HCl suppressed arrhythmias (ventricular contractions of ectopic origin), and hence satisfied the cardinal specification for anti-arrhythmic drugs.

Since it is known that dantrolene sodium can be composed in a variety of pharmaceutical dosage forms, it is within the professional judgement and skill of the practitioner to determine the exact amount and form to be administered.

What is claimed is:

1. A method of treating cardiac arrhythmia in hypothermic and normothermic warm-blooded animals comprising administering to an animal in need thereof an amount of dantrolene sodium effective to treat such arrhythmia.

2. The method of claim 1 wherein the cardiac arrhythmia is a supraventricular tachycardia.

3. The method of claim 1 wherein the cardiac arrhythmia originates from infarcted tissues.

4. The method of claim 1 wherein the cardiac arrhythmia is a ventricular arrhythmia due to reentry.

* * * * *

UNITED STATES PATENT AND TRADEMARK OFFICE
CERTIFICATE OF CORRECTION

PATENT NO. : 4,543,359

DATED : September 24, 1985

INVENTOR(S) : Keith O. Ellis and Alan F. Moore

It is certified that error appears in the above-identified patent and that said Letters Patent are hereby corrected as shown below:

In the specification:

Column 2, lines 54 and 65, "means" should read --mean--, and

Column 2, line 61, "p>0.5" should read -- $p < 0.05$ --

Signed and Sealed this

Thirty-first Day of May, 1988

Attest:

DONALD J. QUIGG

Attesting Officer

Commissioner of Patents and Trademarks